US00PP19809P2

(12) United States Plant Patent
Dofferhoff

(10) Patent No.: US PP19,809 P2
(45) Date of Patent: Mar. 10, 2009

(54) ***GENTIANA* PLANT NAMED 'MAGIC PURPLE'**

(50) Latin Name: *Gentiana makinoi*
Varietal Denomination: Magic Purple

(76) Inventor: Hans Dofferhoff, Middelburgseweg 1, Reeuwijk (NL), 2811 PL ( * ) Notice: Subject to any disclaimer, the term of this patent is extended or adjusted under 35 U.S.C. 154(b) by 0 days.

(21) Appl. No.: 12/069,706

(22) Filed: Feb. 12, 2008

(51) Int. Cl.
*A01H 5/00* (2006.01)

(52) U.S. Cl. ..... Plt./433

(58) Field of Classification Search ..... Plt./433, Plt./263

See application file for complete search history.

*Primary Examiner*—Annette H Para
*Assistant Examiner*—S. B. McCormick Ewoldt
(74) *Attorney, Agent, or Firm*—Penny J. Aguirre

(57) ABSTRACT

A new cultivar of *Gentiana makinoi* named 'Magic Purple', characterized by its large, deep violet blue flowers borne on thick, strong, dark purple-black stems combined with a uniform and upright plant, a vigorous growth habit, and suitability for use as a cut flower.

2 Drawing Sheets

Botanical classification: *Gentiana makinoi.*
Varietal denomination: 'Magic Purple'.

BACKGROUND OF THE INVENTION

The present invention relates to a new and distinct cultivar of *Gentiana makinoi* and will be referred to hereafter by its cultivar name, 'Magic Purple'. 'Magic Purple' represents a new *Gentian,* an herbaceous perennial grown for landscape use.

The inventor discovered the new cultivar, 'Magic Purple', as a chance seedling that arose in a cultivated area in his nursery in Reeuwijk, The Netherlands in the summer of 2005. Although the parentage is unknown, the characteristics of the new cultivar and the presence of the cultivar *Gentiana makinoi* 'Royal Blue' (not patented) in the nursery suggest that 'Royal Blue' is a likely parent.

Asexual reproduction of the new cultivar was first accomplished by in vitro propagation under the direction of the inventor in Rijswijk, The Netherlands in 2005. It has been determined that the characteristics of the new cultivar are stable and are reproduced true to type in successive generations.

SUMMARY OF THE INVENTION

The following traits have been repeatedly observed and represent the characteristics of the new cultivar after observing plants grown outdoors in a field for two years in Reeuwijk, The Netherlands. These attributes in combination distinguish 'Magic Purple' from 'Royal Blue' and all other varieties of *Gentians* known to the inventor.

1. 'Magic Purple' exhibits large, deep violet blue colored flowers.
2. 'Magic Purple' exhibits dark black-purple stems and peduncle.
3. 'Magic Purple' exhibits strong, thick stems.
4. 'Magic Purple' exhibits stems that are uniform in height and about 115 cm in height.

5. The flowering stems of 'Magic Purple' make suitable cut flowers.
6. 'Magic Purple' has a vigorous growth habit.

'Magic Purple' differs from its probable parent plant, 'Royal Blue' in having flowers that are more purple and deeper in color and in having thicker, black-purple stems. 'Magic Purple' can be most closely compared to the cultivar 'Marsha' (U.S. Plant Pat. No. PP16,562). 'Magic Purple' has similar flowers to 'Marsha', however the flowers of 'Magic Purple' are more purple in color and 'Marsha' has a compact vase-shaped plant habit with an average height of 40 cm and stem that are not dark purple in color.

BRIEF DESCRIPTION OF THE PHOTOGRAPHS

The plants and plant parts in the photographs were taken of two-year old plants of 'Magic Purple' as grown outdoors in a field plot in Reeuwijk, The Netherlands.

Figure 1:
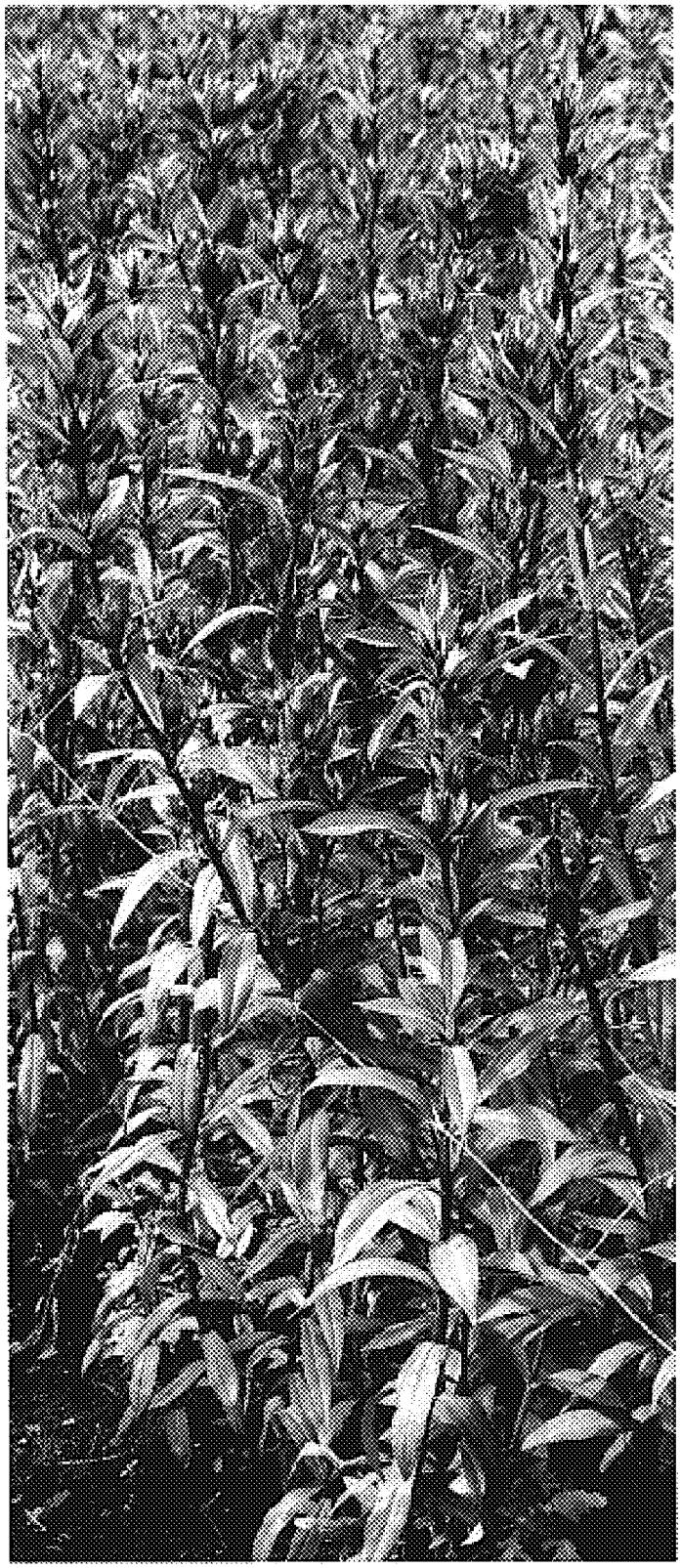

The photograph in FIG. 1 provides an overall view of the new Gentian in bloom.

Figure 2:
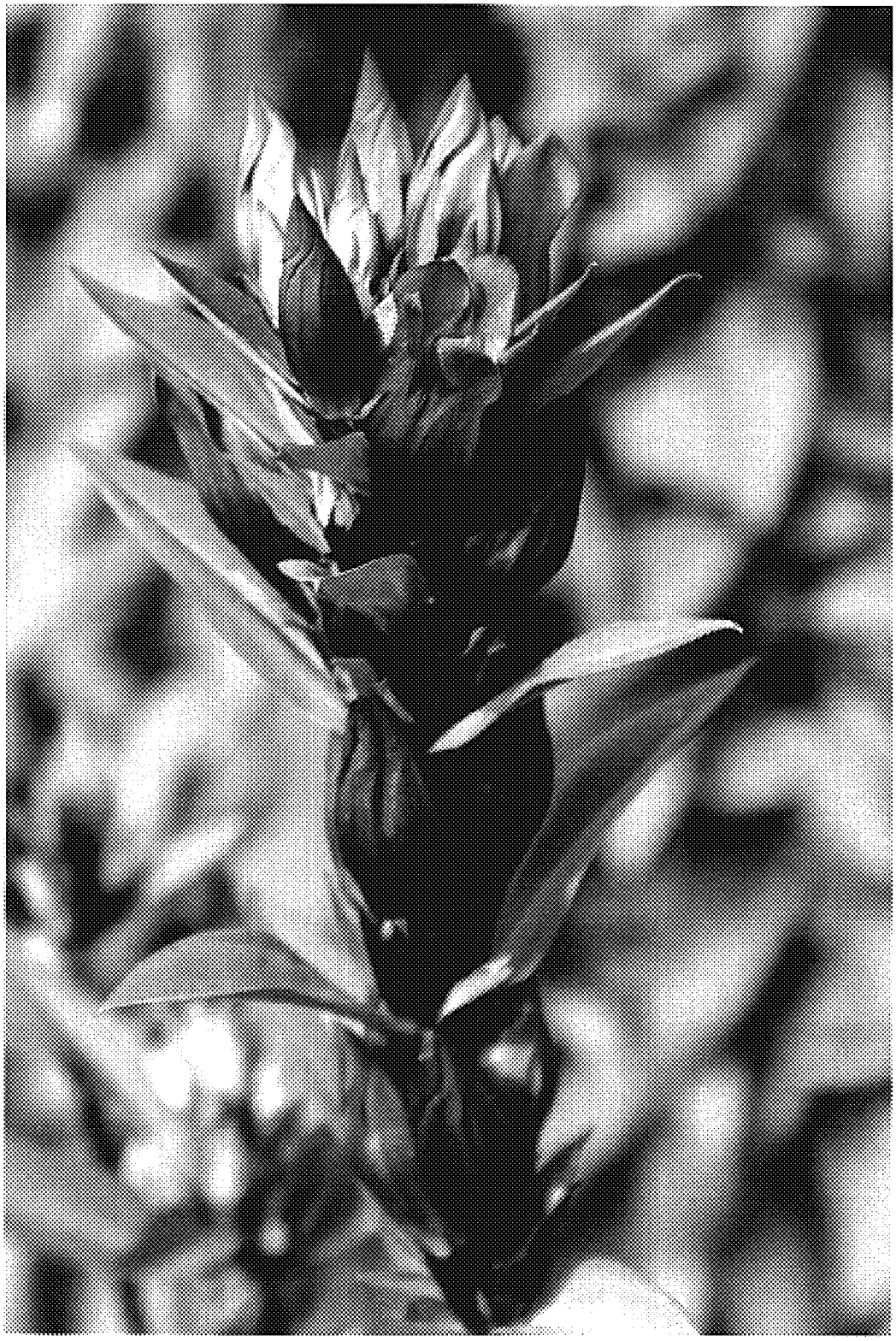

The photograph in FIG. 2 provides a close-up view of the flowers of 'Magic Purple'.

The colors in the photographs are as close as possible with the photographic and printing technology utilized. The color values cited in the detailed botanical description accurately describe the colors of the new *Gentian.*

DETAILED BOTANICAL DESCRIPTION

The following is a detailed description of two year-old plants the new cultivar as grown in a field in Reeuwijk, The Netherlands under natural light with average day temperatures ranging from 15° to 27° C. and average night temperatures ranging from 7° to 18° C. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Blooming period.*—Continuously from mid August to mid September in The Netherlands.

*Plant type.*—Herbaceous perennial.

*Plant habit.*—Clump-forming, narrowly upright, compact, uniform.

*Height and spread.*—Average of 115 cm in height and 45.0 cm in spread.

*Cold hardiness.*—At least to U.S.D.A. Zone 6.

*Heat tolerance.*—At least to 35° C.

*Culture.*—Prefers humus-rich, moist but well-drained soils in partial shade or full sun in areas where summers are cool with sufficient moisture.

*Diseases and pests.*—Not more susceptible than other *Gentiana makinoi* varieties.

*Root description.*—Fine.

Growth and propagation:

*Propagation.*—Stem cuttings and tissue culture.

*Root initiation.*—Roots appear on cuttings in about 10 days when grown at about 25° C. in a greenhouse without supplemental lighting during the summer months.

*Root development.*—Roots fully develop in a 13 cm pots in about 3 months from a rooted cutting.

*Cropping time to bloom.*—About 3 months from a cutting or rooted transplant from tissue culture.

*Growth rate.*—Highly vigorous, growing about 25 cm per month in the spring.

Stem description:

*Stem shape.*—Round.

*Stem color.*—N186C.

*Stem size.*—Average of 110.5 cm in length, average of 7 mm in diameter.

*Stem surface.*—Slightly glossy, smooth.

*Stem aspect.*—Upright, strong.

*Internode length.*—Average of 5.0 cm.

*Branching habit.*—Basal branching with no lateral branching, about 7 unbranched stems emerge from crown.

*No. of harvestable cut flower stems.*—7 per year.

Foliage description:

*Leaf shape.*—Lanceolate to narrowly elliptic.

*Leaf division.*—Simple.

*Leaf base.*—Cuneate.

*Leaf apex.*—Acute.

*Leaf venation.*—Pinnate, only midrib is conspicuous, color on upper surface is 144B, color on lower surface is 144B to 144C.

*Leaf margins.*—Entire.

*Leaf attachment.*—Sessile.

*Leaf arrangement.*—Opposite.

*Leaf surface.*—Dull, slightly leathery, glabrous but slightly glaucous on upper surface.

*Leaf color.*—Young upper surface; 139A, young lower surface; 137D with base 187A, mature upper surface; between 137A and 139A, mature lower surface; 138A to 138B with base 187A.

*Leaf number.*—Average of 48 (24 pairs) per stem.

*Leaf size.*—Average of 10.4 cm in length and 2.6 cm in width.

*Leaf substance.*—Thick, moderate to high durability to environmental stresses.

Flower description:

*Flower type.*—Axillary and terminal tubular flowers, arising singularly or in small clusters.

*Flower fragrance.*—Faint, sweet.

*Flower lastingness.*—Average of 10 days on plant, persistent, 14 days as a cut flower.

*Flower bud description.*—Narrowly elliptic in shape, average of 1.3 cm in diameter and 4.2 in length, color of petal portion is N88B flushed on lower half with N79C, color of calyx portion is 187A to 187B with tips 146B to 146C.

*Flower quantity.*—Average of 40 per stem.

*Flower aspect.*—Held upright.

*Flower shape.*—Urn-shaped with base fused and upper 17% free.

*Flower size.*—5.3 cm in depth and 1.8 cm in diameter.

*Rate of opening.*—About 50% fully open at flowering peak.

*Peduncles.*—1.9 cm in length and 3 mm in diameter with an average angle to stem of 15°, 187A in color, strong, occur on axillary flowers with terminal flowers sessile to stem.

*Pedicels.*—None.

*Petals.*—5, about 4.9 cm in length and 1 cm in width, narrowly oblong in shape, 83% of lower portion is fused into a tubular shape, margin is entire, apex is broadly acute, surface is smooth and slightly glossy in appearance, color (opening and fully open); outer surface 96A to 96B with margin at the apex 93B, middle region flushed 83A and base 157D, inner surface 94B with middle region 97C to 97D, stripes of N92A to N92B and base 157D, fading to N89A with apex 83A and lower half 83B to 83C.

*Calyx form.*—Campanulate in form, average of 3.2 cm in length and 1.4 cm in diameter.

*Sepals.*—5, average of 3.2 cm in length, 2 mm in width, 60% fused with free tips linear in shape, margin is entire, apex is narrow and acute, base is fused, surface is smooth and dull in appearance, color of inner surface 145D with free tips 146B to 146C, outer side is 187A to 187B with free tips 146B to 146C.

Reproductive organs:

*Gynoecium.*—3 pistils, about 3.1 cm in length, stigma is linear and decurrent when ovary develops and 145C in color, style is about 2.9 cm in length 145B in color, ovary is 145B in color.

*Androecium.*—5 stamens, anthers are oblong in shape, basifixed, about 6 mm in length, 1.0 cm in width and 5D in color, filaments are about 2.3 mm in length and 157B in color, pollen is moderately abundant and 4B to 4C in color.

*Seed.*—No seed production has been observed under the conditions tested.

It is claimed:

1. A new and distinct cultivar of *Gentiana makinoi* plant named 'Magic Purple' as herein illustrated and described.

* * * * *